United States Patent [19]
Schubert et al.

[11] Patent Number: 5,756,661
[45] Date of Patent: May 26, 1998

[54] *PENTACLETHRA MACROLOBA* DERIVED SUBSTANCES HAVING INSECTICIDE, AGGLUTINATION AND AMINOPEPTIDASE INHIBITION ACTIVITY

[75] Inventors: Karel R. Schubert; Ulrich Reimann-Philipp, both of Norman, Okla.; Thomas H. Czapla, Urbandale, Iowa; Harold B. Rathburn, Stephenville, Tex.

[73] Assignee: Pioneer Hi-Bred International, Inc., Des Moines, Iowa

[21] Appl. No.: 749,791

[22] Filed: Nov. 15, 1996

[51] Int. Cl.$^6$ .............................. A61K 38/00; C07K 2/00; C07K 4/00; C07K 5/00
[52] U.S. Cl. .................................. 530/300; 514/2
[58] Field of Search ................... 530/300; 514/2

[56] References Cited

PUBLICATIONS

Insecticidal Action of the Phytohemagglutinin in Black Beans on a Bruchid Beetle; Janzen, Daniel H., Science, vol. 1192, May 21, 1976, pp. 795–796.

*Pentaclethra macroloba* Seed effect on Larval Growth, Cell Viability, and Midgut Enzyme Activity of *Helicoverpa zea* (Lepidoptera: Noctuidae); J. of Economic Entomology 87 [6]: 1754–60 (1994).

Toxicity of Secondary Compounds to the Seed–eating Larvae of the Bruchid Beetle—*Callosobruchus Maculatus*—Phytochemistry, 1977, vol. 16, pp. 223–227.

Potentially Defensive Proteins in Mature Seeds of 59 Species of Tropical Leguminosae—Journal of Chemical Ecology, vol. 12, No. 6, 1986.

*Primary Examiner*—Cecilia J. Tsang
*Assistant Examiner*—Jennifer Harle

[57] ABSTRACT

The invention comprises a leucine aminopeptidase inhibitor (LAPI) having hemagglutination activity which is extracted from the seeds of *Pentaclethra macroloba*. The crude extract was found to comprise an active species having a molecular weight in the range 1.5–60 kilodaltons and further comprises an amino acid containing component, a fluorescent component and sugars. The basic unit of the active species contains approximately the following type and number of amino acid residues averaged over a plurality of separations and analyses: 3 aspartate, 3 threonine, 4.5 serine, 3.75 glutamic, 6.5 glycine, 3.5 alanine, 2.25 valine, 1.25 isoleucine, 2 leucine, 0.75 tyrosine, 1.25 phenylalanine, 5.25 lysine, 0.75 histidine, 2.25 arginine and 0.625 proline, and forms multimers, adduct, conjugate and similar species between by itself or with proteinaceous, fluorescent and sugar substance which may also be present. The active substance(s) act as an insecticide and have been found to increase insect mortality in bioassays. The active substance(s) are particularly effective against European corn borer larvae.

8 Claims, 9 Drawing Sheets

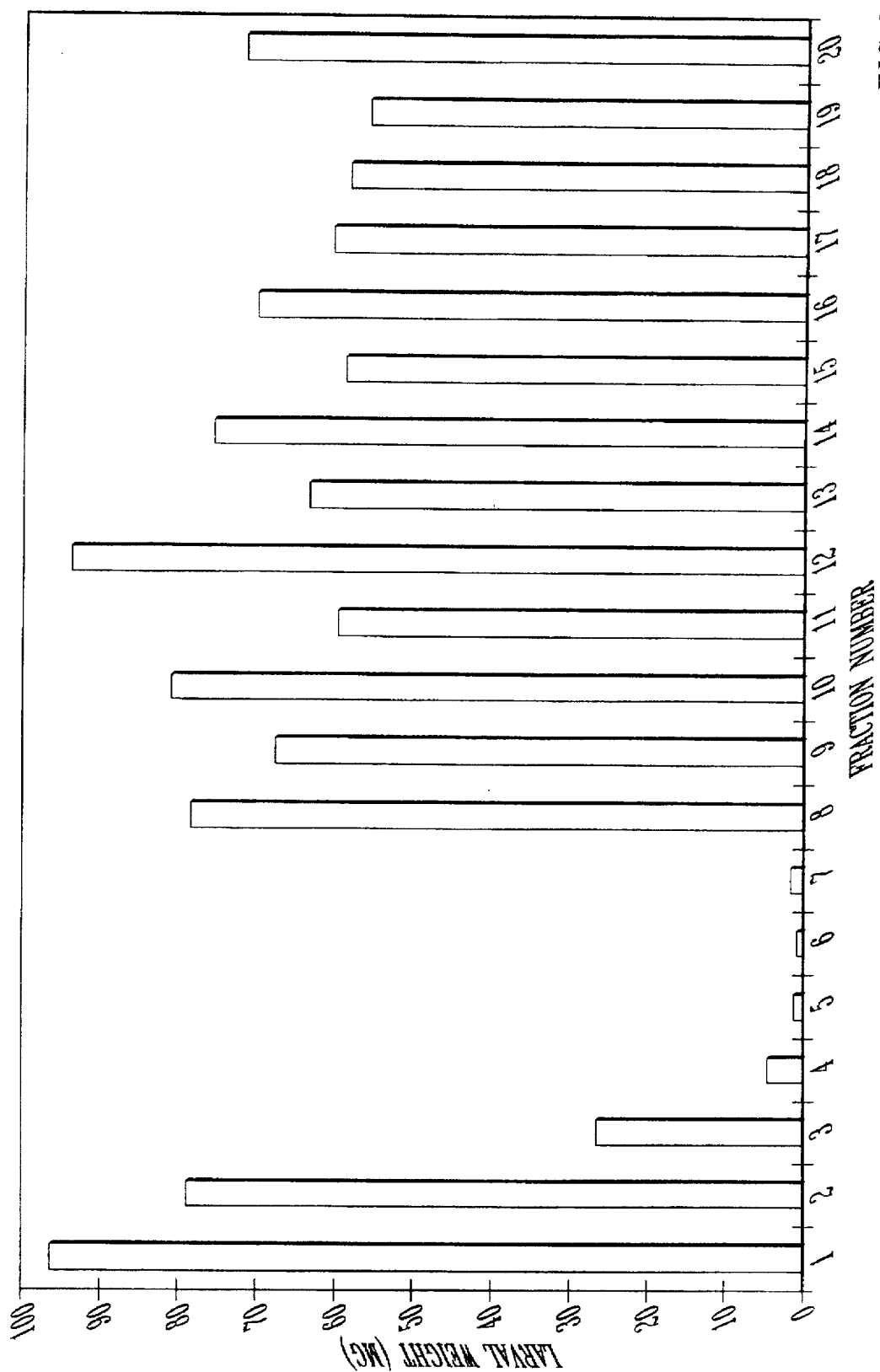

PENTACLETHRA MACROLOBA DERIVED SUBSTANCES HAVING INSECTICIDE, AGGLUTINATION AND AMINOPEPTIDASE INHIBITION ACTIVITY

RELATED APPLICATION

This application is related to copending application Ser. No. 08/560,727, filed Nov. 20, 1995, which is entitled "*PENTACLETHRA MACROLOBA* PROTEIN HAVING INSECTICIDAL PROPERTIES" whose teachings are incorporated herein by reference.

FIELD OF THE INVENTION

The invention relates to methods and materials for controlling insect species. In particular, the invention relates to a substance or mixture of substances extracted from the plant *Pentaclethra macroloba*, which substance or mixture of substances have leucine aminopeptidase inhibition activity and hemagglutinin activity, the latter being a characteristic of lectins, and has been found to exhibit insecticidal activity when applied at levels comparable to *Bacillus thuringiensis* protein endotoxin levels.

BACKGROUND OF THE INVENTION

Numerous insect species are serious pests to common agricultural crops such as corn, soybeans, peas and similar food and fiber crops. During the last century, the primary method of controlling such pests has been through the application of synthetic chemical insecticide compounds. However, as the use of such chemical compounds proliferated and continued, it became evident that such wide-spread use posed problems with regard to the environment, the non-selectivity of the compounds, increasing insect resistance to the chemicals and the effect of such compounds, after run-off, on higher order species such as fish and birds among others. As a result of such problems, other methods of controlling insect pests were sought and tried.

One such alternative method of pest control has been the use of biological organisms which are typically "natural predators" of the species sought to be controlled. Such predators may include other insects, fungi (milky-spore) and bacteria such as *Bacillus thuringiensis*. Alternatively, large colonies of an insect pest have been raised in captivity, sterilized and released into the environment in the hope that mating between the sterilized insects and fecund wild insects will decrease the insect population. While both these approaches have had some success, they entail considerable expense and present several major difficulties. For example, it is difficult both to apply biological organisms to large areas and to cause such living organisms to remain in the treated area or on the treated plant species for an extended time. Predator insects can migrate and fungi or bacteria can be washed off a plant or removed from a treated area by rain. Consequently, while the use of such biological controls has desirable characteristics and has met with some success, in practice these methods seem severely limited. However, scientific advances seem to offer new opportunities for controlling insect pests.

The advances in biotechnology in the last two decades have presented new opportunities for pest control through genetic engineering. In particular, advances in plant genetics coupled with the identification of insect growth factors and naturally-occurring plant defensive compounds or agents offer the opportunity to create transgenic crop plants capable of producing such defensive agents to thereby protect the plants against insect attack.

The resistance of plants to insect or parasite infection relies on a variety of structural and chemical defense mechanisms. These mechanisms can be pre-formed or can be activated upon parasite attack. The plant resistance created by these mechanisms can be limited to specific races of pathogens or can be effective against a broad spectrum of parasitic species. The biochemical and genetic characterization of such defense mechanisms and the chemical substances involved has led to the identification of plant gene sequences that may be used to genetically engineer plants expressing these mechanisms and chemicals.

Transgenic plants that are resistant to specific insect pests are known and have been transgenically created using genes encoding *Bacillus thuringiensis* (BT) endotoxins or plant protease inhibitors (PIs). The resistance of plants through the use of transgenically inserted BT genetic material encoding for BT toxins has been shown to be very effective and the first cultivars expressing this genetic material are now commercially available. Effective plant protection using transgenically inserted PI genetic material has not yet been demonstrated in the field. While cultivars expressing BT genetic material may presently exhibit resistance to pests, resistance based on the expression of a single gene might eventually be lost due to the evolution of BT resistance in the insect pests. Consequently, the search continues for additional genetic material which can be transgenically inserted into plants to provide them protection against insect pests.

Scientists have identified some specific plant components or compounds which act as defensive agents to protect a plant from attack by insect pests and pathogens. While such components are usually present at only low levels in various plant tissues, some of them are also capable of being induced to higher levels upon attack by an insect pest or a pathogen. Examples of such defensive compounds include alkaloids, terpenes and various proteins such as enzymes, enzyme inhibitors and lectins (14, 24, 27 and 28). Of particular interest are plant derived compounds which can block or alter normal biomolecular activity and thus inhibit insect growth or kill the insect. For example, trypsin is a digestive enzyme secreted by the midgut cells into the endo and exo peritropic space, and leucine aminopeptidase (LAP) is a digestive enzyme. The role of both in the body is to hydrolyze polypeptides into smaller units which can then be utilized by the host subject, for example, an insect. An enzyme such as trypsin which catalyzes the hydrolysis of peptide bonds is called a protease. Blocking trypsin activity will inhibit insect growth. A trypsin inhibitor (abbreviated TI) or leucine aminopeptidase inhibitor (herein abbreviated LAPI) is thus a compound which will block or decrease trypsin or leucine aminopeptidase protease activity, respectively. As a result of such blockage or decrease in trypsin or LAP protease activity, a host subject which has ingested TI or LAPI with its food will obtain liffle or no benefit from the polypeptides contained in the food. The host may thus fail to grow, mature and may indeed ultimately starve and die.

Plant lectins are group of proteins which may stimulate mitosis, a process which takes place in the nucleus of a dividing cell, involves a series of steps (prophase, metaphase, anaphase and telophase), and results in the formation of two new nuclei, each of which have the same number of chromosomes as the parent nucleus. The lectin molecule binds to specific receptors on the cell surface, possibly analogous to or identical to the receptor sites on the cell surface which normally bind certain hormones such as insulin (whose action lectins can mimic on some cells). Once the lectin is bound, a molecular signal is set off within the cell which greatly effects the rate of cell division and the tendency to differentiate.

One of the best known lectins is wheat phytohemagglutinin which is so named because it agglutinates red blood cells. Red blood cell agglutination is a rather general property of lectins. Introduction of a lectin into blood samples causes the red blood cells to cluster together. In a host such as an insect, this would effectively remove the cells from their role of transporting oxygen and/or cause blockage of the smaller arteries and veins, and effectively result in the insect's death. Agglutination reactions also serve as an analytical tool. Properly performed, agglutination reactions have a high degree of sensitivity and can detect an enormous variety of substances. Inhibition of agglutination is likewise important. If carefully standardized using highly purified substances, inhibition of agglutination can be used as an indicator of the amount of a substance, typically an antigen or antibody, in animal, including human, or plant tissue or cells. [Agglutination and techniques: see D. P. Stites et al., Basic & Clinical Immunology, 6th Ed. (Appleton & Lange, Norwalk, Conn., 1987), pages 274–277.]

Aminopeptidases are proteases which remove the N-terminal amino acid of polypeptides. They are found in a wide variety of animals (12) and some plant species (8) at various locations in the subject such as the midgut in insects (4, 7) and mammalian kidneys, liver and lens (12). The aminopeptidases are classified according to the N-terminal amino acid the enzyme prefers and they commonly contain a divalent metal ion, usually $Zn^{+2}$. On the cellular scale, aminopeptidases have been found in the cytosol, various organelles and as components of the cellular membrane (12).

Aminopeptidases have been implicated in a variety of biological functions. For example, they are believed to enhance cell-mediated immunity (2), and to be involved in the regulation of hormones and the digestion of polypeptides (12) in food. They are also believed to play a role in some human diseases such as hypertension (3) and cancer (10). Especially important among aminopeptidases, at least from a digestive viewpoint, is leucine aminopeptidase (LAP), an exopeptidase which has a preference for leucine-terminated polypeptides or proteins as described by Taylor (12). LAP isolated from porcine liver has an estimated molecular weight of 318 kilodaltons (kDa) and is composed of at least six subunits of 35 kDa molecular weight.

The art has shown that there are, in microbes and animals, naturally occurring compounds which inhibit the activity of aminopeptidases. Two such aminopeptidase inhibitors, bestatin and amastatin, have been isolated from microbial sources such as Streptomyces sp. These two inhibitors are small peptides which have been shown to completely inhibit the activity of several aminopeptidases (13, 1). Synthetic aminopeptidase inhibitors such as aminophosphonates (6) and catechoyl-dipeptides (9) are also known. However, until the disclosure of the instant invention, the art has not previously known or shown that aminopeptidase inhibitors are present in and can be isolated from plants.

An ideal source of plant species to investigate for potential inhibitory substances is the tropical forests. The diversity of tropical forest plant and insect life provides an ideal evolutionary background for the development of inhibitory substances. For example, a given tropical plant species might be the subject of attack by a variety of insect species. Consequently, the plant may develop a particularly strong or effective inhibitory substance for use as a protective agent against such a diversity of insect life. Janzen et al. (19), studying trypsin inhibition and lectins, investigated seeds from 59 legumes from the tropical dry forest and showed that while all were capable of inhibiting bovine trypsin, they did so at different levels. Likewise, the presence and levels of lectins varied with seeds of different species. That is, some were stronger inhibitors than others. One such tropical plant not tested by Janzen was the legume *Pentaclethra macroloba* (hereinafter *P. macroloba* or Pm, (17)). Recently, Chun et al. (29) showed that aqueous seed extracts from *P. macroloba* had an inhibitory effect on insect herbivores.

The LAPI substance disclosed herein is believed to be the first aminopeptidase inhibitor isolated from a plant source. The results shown herein indicate that it effectively kills insects when administered at microbial *Bacillus thuringiensis* (BT) insecticidal protein levels. The LAPI substance described herein appears to be the most effective non-BT insecticidal protein ever isolated. The toxicity of the Pm derived toxin was retained in dialysis tubing and could be precipitated with ammonium sulfate. This suggests that the toxicity is caused by a protein, a proteinaceous substance or a mixture containing a proteinaceous substance rather than low molecular weight secondary metabolites. In addition, the Pm extracts were found to cause the agglutination of rabbit and human blood cells. No similarity to known agglutinins was found. The active substance(s) in the Pm extract are apparently comprised of a protein, a proteinaceous substance or an amino acid containing substance, an ethidium bromide binding substance, a fluorochrome of as yet unidentified nature, and sugars including glucose, rhamniose and arabinose.

The purpose of the present invention is to identify and characterize one or a plurality of substances which are not trypsin inhibitors and which are obtainable from *P. macroloba*, said substance(s) reducing insect growth, increasing insect mortality, agglutinating red blood cells and inhibiting leucine aminopeptidase activity.

It is a further purpose of the invention to provide a method for the separation and isolation of such substance(s) obtainable from *P. macroloba* and to demonstrate the inhibitory nature of such inhibitory substance.

It is a further purpose of the invention to identify an antinopeptidase inhibitor which has sufficient insect growth inhibitory effects to warrant the genetic sequence producing the inhibitor being transgenically inserted into a food crop gene where it will be expressed and will provide protection from one or a plurality of insect species including, but not limited to, European corn borer (*Ostrinia nubilalis*), Diabrotica species such as the Western, Southern and Northern corn rootworms, corn earworm (*Helicoverpa zea*), cowpea weevil (*Callosobruchus maculatus*) and similar insect pests known to those skilled in the art.

It is a further purpose of the invention to identify one or a plurality of substances which exhibit red blood cell agglutination activity.

It is a further purpose of the invention to identify one or a plurality of substances which have an inhibitory effect on digestive or regulatory enzymes, and in particular on the activity of leucine aminopeptidase.

SUMMARY OF THE INVENTION

The invention identifies and provides one or a plurality of substance(s) obtainable from *Pentaclethra macroloba* which have a molecular weight in the range 1.5 to 60 kilodaltons (kDa) in size; said substance being designated herein as either LAPI or Pentin-2.

The invention is also directed to one or a plurality of purified insecticidal substance(s) obtained from *Penta-* clethra macroloba by a method comprising the steps of extracting sliced, crushed or powdered Pentaclethra macroloba seeds, extracting said sliced, crushed or powdered seeds with an aqueous solution to obtain a crude extract having one or a plurality of substance(s) which increase insect mortality, inhibit leucine aminopeptidase activity, have lectin hemagglutinin characteristics and a molecular weight in the range 1.5 to 60 kDa; said substance or plurality of substances comprising protein or amino acid containing material, an ethidium bromide binding substance, an unknown fluorochrome and various sugars.

The invention is further directed to a process for protecting plants against insect attack by European corn borer, Helicoverpa zea, corn rootworms and similar insects by exposing said insects to an insecticidal substance obtained from P. macroloba, said insecticidal substance being a non-trypsin affecting substance contained within a crude or purified extract of P. macroloba seed and identified as having one or a plurality of active components whose molecular weights are in the range 1.5–60 kDa. The insecticidal substance of the invention may be topically or systemically applied to a plant using methods and means known to those skilled in the art. The insecticidal substance of the invention may be produced by a plant into which has been inserted genetic material encoding the P. macroloba insecticidal substance disclosed herein.

BRIEF DESCRIPTION OF THE DRAWINGS

FIG. 9 illustrates the inhibition of insect growth resulting from the application of the various fractions separated on a Superose 12 column as described in Example 1.

DETAILED DESCRIPTION OF THE INVENTION

References

Figure 1:
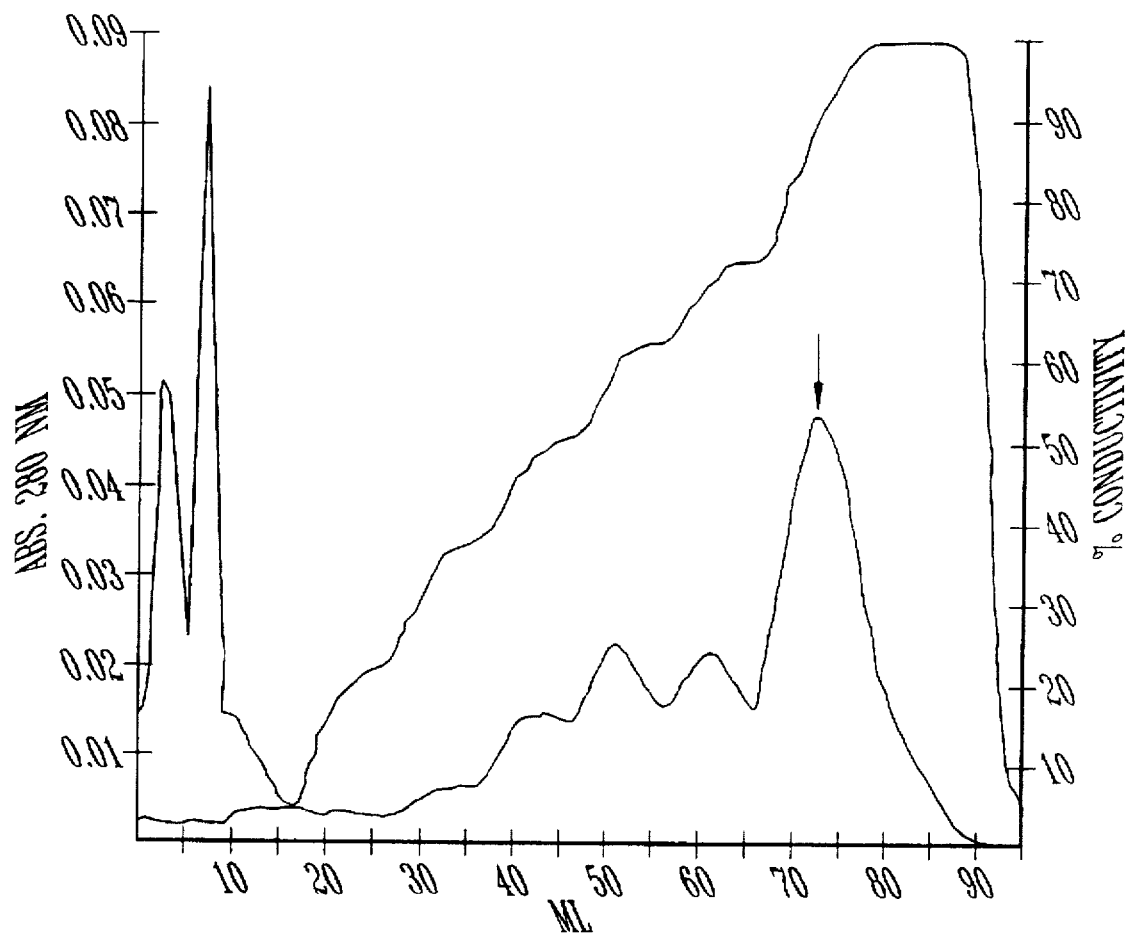
FIG. 1 illustrates a hydrophobic interaction chromatograph of a P. macroloba extract obtained using a phenyl Sepharose coluim and indicates with an arrow the position of the peak containing the substance(s) having agglutination and LAPI activity, and capable of increasing insect mortality.

The teachings of the following publications, which are known to those skilled in the art of the field of the invention, are incorporated herein by reference.

1. T. Aoyagi et al., J Antibiotics 31: 636–638 (1978); amastatin, an aminopeptide inhibitor.
2. R. K. Barclay et al., Biochem Biophys Res. Commun., 96: 1732–1738(1980); inhibition of enkephalin-degrading aminopeptidase activity by selected peptides.
3. O. A. Carretero et al., Hypertension 68: 366–371 (1991); the use of metallopeptidase inhibitors for treating hypertension.
4. J. G. Houseman et al., Insect Biochem. 17: 213–218 (1987); a preliminary characterization of the digestive proteases in the posterior midgut of the stable fly Stomoxys calcitrans (Diptera: muscidae).
5. C. A. Lee et al., Anal. Biochem. 166: 308–312 (1987); copper staining used in sodium dodecyl sulfate—polyacrylamide gels.
6. B. P. Lejczak et al., Biochem. 28: 3549–3555 (1989); inhibition of aminopeptides by aminophosphonates.
7. C. J. Lenz-Goodman et al., Archives Insect Biochem. Physiol. 16: 201–212 (1991); the digestive proteases of the larvae of corn earworm, Heliothis zea: characterization, distribution and dietary relationships.
8. L. Mikola and J. Mikola, Plant Proteolytic Enzymes, ed. M. J. Dalling, (CRC Press, Boca Raton, Florida 1986 ), Vol. 1, pages 97–117.
9. L. J. Nakonieczna et al., Z. Naturforsch. 44b: 811–816 (1989); catechoyl-dipeptides as leucine aminopeptidase inhibitors.
10. K. Ota, Biomed Pharmacol. 45: 55–60 (1991), a review of bestatin clinical research.
11. H. Schagger et al, Anal. Biochem. 166: 368–379 (1987); describes the use of tricine-SDS-PAGE to separate proteins in the 1–100 kDA range.
12. A. Taylor, FASEB, J 7: 290–298 (1993), describing the structure and function of aminopeptidases.
13. H. T. Umezawa et al., J Antibiotics 29: 97–99 (1976), bestatin, an aminopeptidase inhibitor.
14. L. T. Baldwin, Oecologia 75: 367–370 (1990).
15. J. T Christeller et al., Insect Biochem. 19: 233–241 (1989).
16. B. C. Hammer et al., Phytochemistry 28: 3019–3026 (1989).
17. G. S. Hartshorn in Costa Rica Natural History, Janzen Ed. (Univ. Chicago Press, Chicago 1983), pages 301–303.
18. V. A. Hilder et al., Nature 330: 160–163 (1987).
19. D. H. Janzen et al., J Chem. Ecol. 12: 1469–1480 (1986).
20. R. Johnson et al., Proc. Natl. Acad. Sci. 86:9871–9875 (1989).
21. U. K. Laemmli, Nature 227: 680–685 (1970).
22. G. Pearce et al., Plant Physiol. 102: 639–644 (1993).
23. H. Rathburn et al., J Econo. Ento. Submitted (1996).
24. C. A. Ryan, Ann. Rev. of Phytopathol. 28: 425–449 (1990).
25. Ureil et al., Nature 218: 578–580 (1968).
26. T. H. Czapla and B. A. Lang, J Econo Ento. 83 (6): 2480–2485 (1990).
27. M. J. Chrispeel et al., Plant Cell 3: 1–9 (1991).
28. D. H. Janzen et al., Phytochemistry 16: 223–227 (1977).
29. J. Chun et al., J Econo Ento. 87: 1754–1760 (1990).

Terminology and Abbreviations

1. TI=trypsin inhibitor.
2. pI=the pH of a solution containing a molecule at which there is no charge on that molecule.
3. IEF=Isoelectric focusing.
4. SDS-PAGE=Sodium dodecyl sulfate-Polyacrylamide gel electrophoresis.
5. NaOAc=sodium acetate.
6. Tris-Cl 32 Trizma base molecular biology reagent.
7. LAP=leucine aminopeptidase.
8. LAPI=leucine aminopeptidase inhibitor of the invention.
9. BT—*Bacillus thuringiensis*.
10. Pentin-2 =the leucine aminopeptidase inhibitor which exhibits agglutination activity and increases insect mortality as disclosed herein.

While various procedures may be used to separate and isolate the active substances comprising the invention, the examples given herein describe the preferred procedures for so doing. Additional methods, all of which use the crude *P. macroloba* extracts, include a combination of ion exchange chromatography, dialysis and other techniques. *P. macroloba* seeds were collected from the lowland tropical plain forest of Costa Rica and transported to the inventors' laboratories where they were sliced, lyophilized and stored at −20° C. prior to use.

Those skilled in the art, while observing that the claimed invention may be suitable for encoding into the genetic code of plants, will also recognize that the active substance(s) of the invention can be formulated for topical or systemic application to plants in order to afford such plants insect protection.

EXAMPLE 1.

Active fractions from *Pentaclethra macroloba* were purified using bioassay-directed and biochemically-directed approaches. Initially, crude and dialyzed extracts of *Pentaclethra macroloba* were tested for their effects on neonate ECB larvae. Seeds of *P. macroloba* were homogenized in cold 10 mM sodium phosphate buffer, pH 7.5. Insoluble polyvinylpyrrolidone was added to the extract to help remove phenolic compounds. The extracts were either filtered through Miracloth and centrifuged to remove debris and other insoluble materials, or simply centrifuged. The supernatant fluid was filtered to remove lipids and other materials which did not pellet during centrifugation. The crude extract was dialyzed extensively against 10 mM sodium phosphate buffer, pH 7.5, at 4° C. over a period of two to four days. During this time, additional proteins and other materials precipitated. These insoluble materials were removed by centrifugation at 18,000 rpm in a Sorvall SS34 rotor at 4° C. prior to use of the material for ECB bioassays. Both crude extracts and dialyzed extracts caused reduction in insect growth and development, and increased insect mortality when incorporated into an artificial diet or overlaid on the diet upon which the ECB larvae were reared. The activity was moderately heat stable.

The active components present in *P. macroloba* seed extracts were fractionated and purified by conventional methods of protein purification. In some instances, dialyzed extracts were heated prior to further fractionation to remove some proteins. Extracts were heated in a water bath at 70° to 100° C. for one to five minutes. After heating, the extract was cooled rapidly on ice and centrifuged at 18,000 rpm in a Sorvall SS34 rotor at 4° C. to remove denatured proteins. Proteins present in the heated and/or dialyzed extracts were concentrated either by ammonium sulfate precipitation or by centrifugal concentration in Centricon filters. For ammonium sulfate precipitation, solid enzyme grade ammonium sulfate was ground to a fine powder with a mortar and pestle. The ammonium sulfate was added very slowly to the extract and stirred with a magnetic stirrer. The extract was maintained in an ice bath at all times. The ammonium sulfate was added to a final concentration of 0.6 g ammonium sulfate per ml of extract. After all of the ammonium sulfate was added, the extract was kept on ice for 15–30 minutes to allow the proteins to precipitate. At this time, the precipitated proteins and other materials were collected by centrifugation at 18,000 rpm in a Sorvall SS34 rotor at 4° C. The pellet was resuspended in a minimal amount of 10 mM sodium phosphate buffer, pH 7.5. Extracts were concentrated in Centricon filtration devices according to the manufacturer's instructions.

Figure 8:
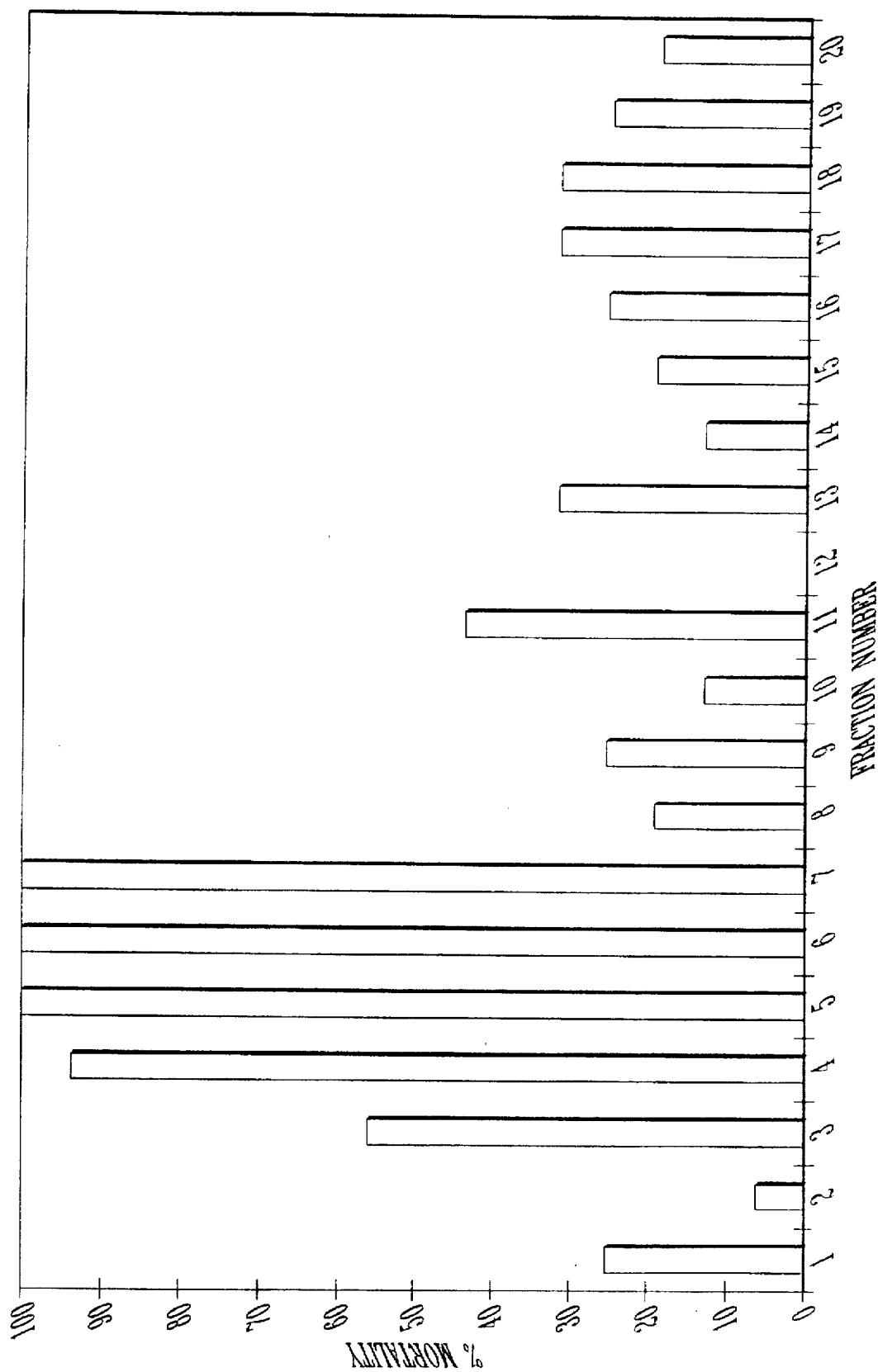
FIG. 8 illustrates insect mortality resulting from the application of the various fractions separated on a Superose 12 column as described in Example 1.

The concentrated proteins and associated materials were applied to a size exclusion column packed with either Sephacryl 200 or Superose 12, Prep grade. The volume of the packed columns were approximately 100 ml. The column was equilibrated with about five volumes of 10 mM sodium phosphate buffer, pH 7.5. Sample was applied in a volume of 0.5 to 1 ml. Proteins and other constituents were eluted with 10 mM sodium phosphate buffer, pH 7.5. Twenty fractions were collected and tested for their effects on ECB larvae. Protein concentrations were estimated using the Bradford assay. Results of ECB bioassay from a typical fractionation of *P. macroloba* seed extracts are shown in FIGS. 8 and 9. Several fractions caused very high mortalities (FIG. 8) and prevented growth of the neonate larvae (FIG. 9). The active component was designated Pentin 2.

Extracts were also fractionated by anion-exchange chromatography on Pharmacia Q Sepharose Fast Flow as the media and using standard methods known to those skilled in the art. A 10-ml column was packed with Q Sepharose and washed extensively in low-salt and high salt buffers. In general, 25 mM Tris-HCl buffer was used as the primary chromatography buffer in the pH range from 8.0 to 9.0, although other buffers were used for chromatography at other pH's. The following is an example of the normal methods used for ion-exchange chromatography.

The column was equilibrated with 25 mM Tris-HCl buffer, pH 8.0. Sample was dialyzed at 4° C. into 25 mM Tris-HCl buffer, pH 8.0, with several buffer exchanges. Sample was applied to the column and all fractions from the column were collected. After all the sample was on the column, the column was washed with 25 mM Tris-HCl buffer, pH 8.0 until most of the unbound protein was washed from the column. Proteins bound to the column were eluted with a linear or step gradient of sodium chloride in 25 mM Tris-HCl buffer, pH 8.0. Fractions were collected and tested for their effects on ECB larvae. Protein concentrations were estimated using the Bradford assay. Results of fractionation by anion-exchange chromatography are not shown.

Fractions from size-exclusion chromatography were subjected to analysis on 12% SDS polyacrylamide gels. Fractions from ion-exchange chromatography were first dialyzed into 10 mM Tris-HCl, pH 8.0 to remove salts and then subjected to SDS-PAGE. Gels were either stained with Coomassie Blue R250 using standard protocols or silver stained. Fractions demonstrating activity against ECB larvae contained only one or two faint protein bands. The native molecular weight of the active material was estimated by size-exclusion chromatography. Based on this analysis, the active component had a molecular weight in the range of 40–60,000 Daltons. Seed extracts were also fractionated based on the ability to inhibit leucine aminopeptidase and to agglutinate red blood cells.

FIGS. 8 and 9 illustrate the effects of highly purified Pentin 2 on the growth and survival of ECB larvae. Pentin 2 was extensively purified as described on a Superose 12 column. Fractions were collected and a 100 μl sample from each fraction applied to the surface of the diet in each well and allowed to dry. Two neonate larvae were placed on the diet in each well and 8 wells were used per treatment. The weight of the larvae and mortality were recorded after 7-10 days. Several fractions showed increased insect mortality, the highest mortalities being shown by factions 3-7.

EXAMPLE 2.

This example and Example 3 were directed to determining the leucine aminopeptidase and agglutination activities of the substance of Example 1, and to show that the same substance is responsible for all three effects. Seed extract was prepared as described by Rathburn et al. (23) with and without heating as noted herein. Heating was accomplished by boiling sliced seeds in 0.1 M Tris-Cl, pH 8.5, 5 mM $MgCl_2$ before homogenization. Briefly, the seeds were homogenized in buffer with polyvinylpyrrolidone. The extract was filtered and centrifuged. The supernatant fluid was heated at 70° C. and subjected to trypsin affinity chromatography (TAC) to remove trypsin inhibitors. The resulting eluant was lyophilized, resuspended in distilled water and dialyzed using a 3,500 molecular weight cut-off (MWCO) membrane against 10 mM NaCl to remove low molecular weight metabolites. TAC was performed according to the method of Rathburn (23). Absorbance at 280 nm (nanometers) was used to follow the elution of the bound proteins.

A sample of the dialyzed material containing 40 mg of protein was separated into components by preparative isoelectric focusing (IEF) using the Rotofor system (Bio-Rad). The Rotofor separates molecules on the basis of their pI or isoelectric point. Every molecule will have a specific net charge, either positive, negative or zero, at a specific pH. The Rotofor, using an electrical current, moves molecules through a pH gradient until they reach their pI; i.e., the pH at which they have zero net charge. The molecule stops migrating at its pI because it is no longer affected by the electrical current. The focusing chamber of the Rotofor is separated into twenty (20) smaller chambers by permeable membranes. These twenty samples are removed simultaneously to ensure as little mixing as possible.

The sample was placed in the focusing medium, a buffered solution (see manufacturer's instructions) which included 12.5% (w/v) glycerol and 2.5% of pH 3-10 Ampholytes (Bio-Rad). After focusing, the fractions were collected, the pH of each determined and each fraction was then dialyzed against 1 M NaCl using a 3,500 MWCO membrane to remove the Ampholytes. The samples were then dialyzed against deionized water to remove the NaCl. Each fraction was lyophilized, resuspended in 0.4 ml of 10 mM NaCl. Fifteen microliters of each fraction was then analyzed using denaturing 12-20% gradient SDS-PAGE (for estimating molecular weight and determining purity) and tested for LAP inhibition and agglutination activity. Most of the agglutination activity and LAP inhibition were found in the acidic fractions. Those fractions with the strongest agglutination activity were also found to be most effective in causing ECB mortality in the bioassays. Fractions that showed LAP inhibition were pooled and further purified by the addition of ammonium sulfate to 75% saturation. The ammonium sulfate preparation was then centrifuged at 10.000 g and 4° C. for 10 minutes. The supernatant liquid was first dialyzed against 10 mM NaCl and then subjected to ion exchange chromatography.

Ion exchange chromatography was used to separate inhibitors from other fractions. A 1.5 ×5.0 cm column containing Q5 Sepharose (Pharmacia) was prepared and equilibrated using 25 mM Tris-Cl, pH 8.0. The column was eluted using a linear gradient of 0 to 0.15 M NaCl. Five milliliter fractions were collected at a flow rate of 1.5 ml/min, the elution being monitored at 280 nm, and the fractions tested for LAP inhibition. Fractions that showed inhibition were pooled, dialyzed against deionized water, lyophilized, dissolved in PBS buffer, pH 8.0, and subjected to gel filtration chromatography to separate the inhibitors from other fractions based on their size. The molecular weight, estimated by gel filtration chromatography, was 45-55,000 Daltons.

Proteins were assayed using the bicinchoninic acid (BCA) system (Pierce. Ref. 22). Bovine serum albumin was used as the standard.

SDS-PAGE, using Rotofor fractions which exhibited inhibitory activity, was used to separate components and determine their subunit molecular weights. The procedure was carried out according to the method of Laemmli (21) using two types of gel, a 12 or 15% acrylamide gel or a 10-20% gradient acrylamide gel. Protein samples were denatured by boiling for three minutes in SDS buffer (BioRad) with 3 mM 2-mercaptoethanol prior to their placement on the gel. For analysis of polypeptides with a molecular weight less than 10 kDa, the discontinuous method of Schagger et al. (11) was employed. After electrophoresis, the proteins were detected by staining with Coomassie Brilliant Blue 250 (12), silver staining or reverse copper staining (5). A band which corresponds with the activity was detected on an SDS-PAGE gel stained with copper. The subunit molecular weight of the substances which exhibit LAP inhibition activity, agglutination, and ECB mortality effects as described and claimed herein was determined by SDS-PAGE to be the range 1.5-10 kDa.

It was noted that different procedures seemingly give different molecular weights. However, it is here noted that the active substance described herein seems capable of forming a complex, conjugate, adduct or a multimeric species with itself or with another substance, presumably proteins or proteinaceous material and sugars, which may be present in a Pm extract. These multimers, conjugates, etc., when characterized by molecular weight determining methods and some separatory techniques, may separate or appear as species having molecular weights over 10 kDa or under 10 kDa. However, all such multimers, conjugates, etc., exhibit insecticidal properties. Consequently, for some applications such a topical spraying, it may not be necessary to use the "purified" insecticidal substance. One may use a crude extract or other preparation which contains such complex, conjugate, adduct, multimer, or similar species.

The above observation explains why one finds that gel filtration or size exclusion chromatography indicates a molecular weight in the range 40-60 kDa and SDS-PAGE gives results in the range 1.5-10 kDa. The 40-60 kDa species may be a multimeric species comprising many units of the active component and possibly other components such as, for example, sugars.

Leucine aminopeptidase inhibition was assayed using two units of porcine kidney LAP (cytosol, type III-CP, EC 3.4.11.1) containing 0.1 M Tris-Cl, 5 mM $MgCl_2$, pH 9.5, at 25° C. in a final volume of 1 ml. The reaction was initiated by the addition of 27 μl of 40 mg/ml L-leucine p-nitroanilide dissolved in dimethyl sulfoxide (DMSO). The increase in absorbance at $A_{410}$ was followed for five minutes. To measure inhibition, an aliquot of the Pm-derived LAP inhibitor was added to the porcine kidney LAP preparation prior to the addition of the substrate. The volume of the buffer was adjusted accordingly. Percent inhibition was determined as described by Rathbun et al. (23).

Figure 6:
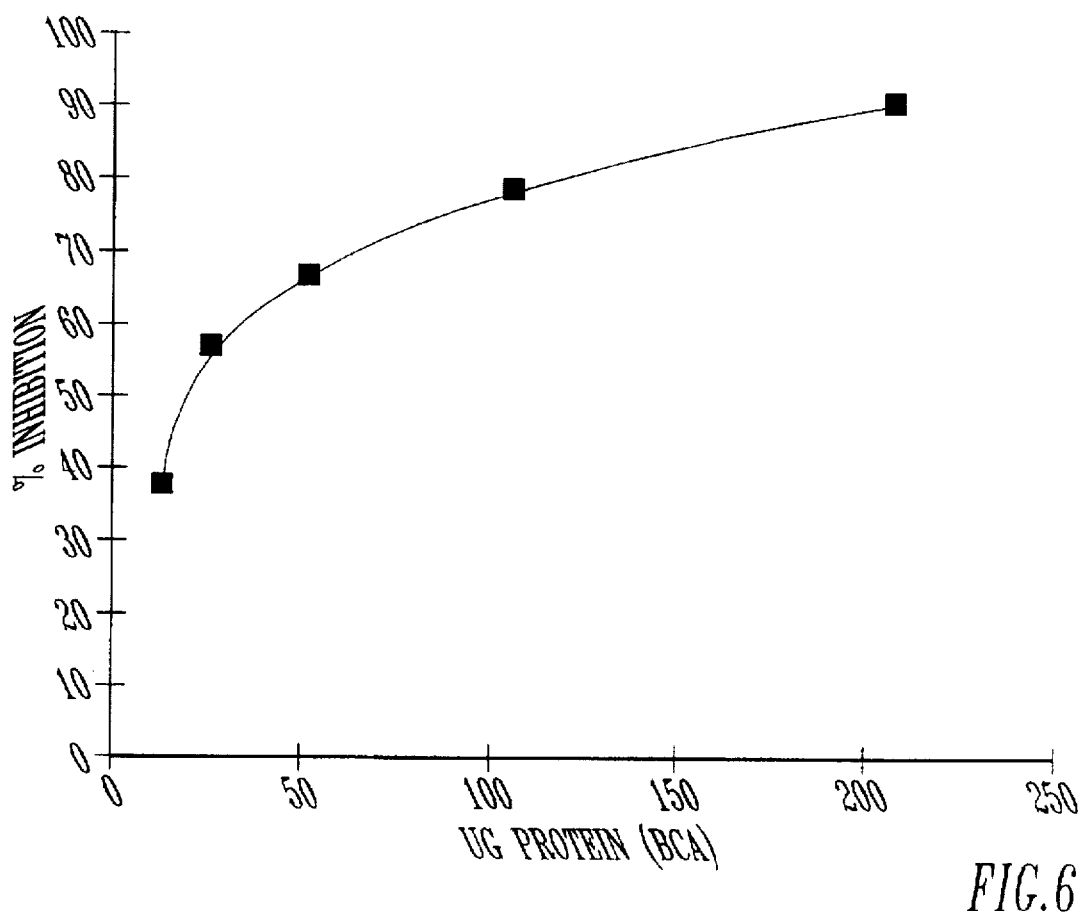
FIG. 6 illustrates the inhibition of 10 μg porcine kidney leucine aminopeptidase by different quantities of the active substance(s) of the invention collected after purification and separations using isoelectric focusing and hydrophobic interaction chromatography.
Figure 7:
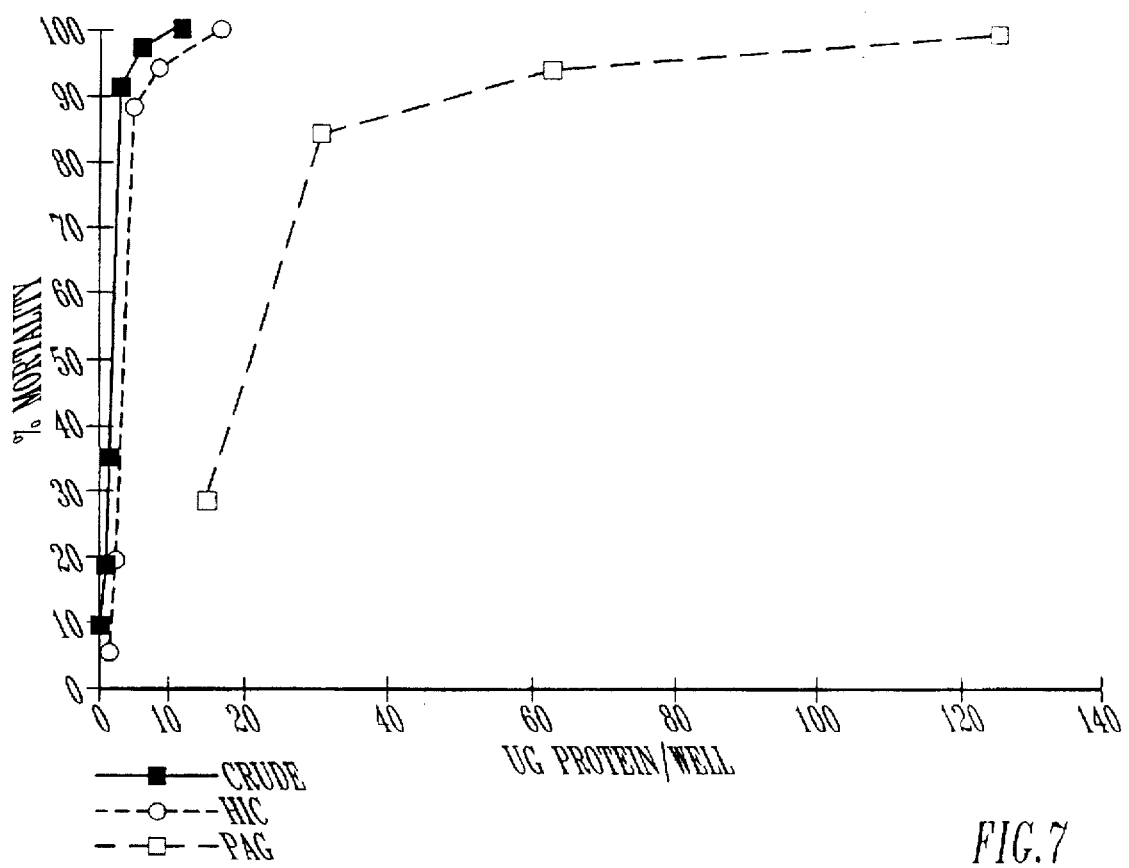
FIG. 7 graphically illustrates the toxicity of the active substance(s) obtained from P. macroloba to European corn borer larvae after seven days. "Crude" signifies extract after removal of particulate matter with or without trypsin affinity chromatography to remove trypsin inhibitors. "HIC" signifies extract obtained after hydrophobic interaction chromatography. "PAG" signifies extract obtained after preparative, non-denaturing acrylamide gel electrophoresis.

Normally, the inhibition of a protease by an inhibitor exhibits a linear relationship and the effectiveness of an inhibitor is measured by the amount required to achieve 50% inhibition. The crude LAP inhibitor which was isolated from *Pentaclethra macroloba* seeds behaved quite differently. The LAPI extract obtained from *P. macroloba* inhibited porcine LAP linearly until about 35% inhibition whereupon the percent inhibition relative to increasing amounts of inhibitor began to plateau. To achieve 50% inhibition would have required very large amounts of crude inhibitor and would not have been a realistic expression of inhibition. Consequently, 20% inhibition, approximately the midpoint of the linear portion of a percent inhibition curve, was chosen to express the effectiveness of inhibition during the early steps of purification. Highly purified LAPI inhibited LAP activity as shown in FIG. 6.

Table 1 gives the LAP inhibition results which were obtained using the twenty Rotofor LAPI fractions obtained in a single Rotofor separation. The results, which are repeatable over numerous tests, indicate the LAPI protein is focused in the acidic region and concentrated mainly in Fractions 1–5. Fraction 1 always yields the largest amount of protein and consequently has the greatest amount of activity per Rotofor unit volume. The results indicate that the *P. macroloba* LAP inhibitor has pI equal to approximately 3.

TABLE 1

Rotofor Fractions, Their pH, % LAP Inhibition and Relative Agglutination

| Rotofor Fraction | pH | μg protein | % LAP Inhibition | Relative Agglutination |
|---|---|---|---|---|
| 1 | 3.21 | 1375 | 54.5 | + |
| 2 | 3.65 | 985 | 48.0 | ++ |
| 3 | 4.18 | 930 | 46.8 | +++ |
| 4 | 4.56 | 755 | 43.4 | +++ |
| 5 | 4.93 | 660 | 38.7 | ++ |
| 6 | 5.37 | 385 | 11.1 | ++ |
| 7 | 5.73 | 375 | 8.4 | ++ |
| 8 | 6.05 | 355 | 4.1 | + |
| 9 | 6.37 | 350 | 3.8 | + |
| 10 | 6.69 | 375 | 2.2 | 0 |
| 11 | 6.95 | 400 | 0 | 0 |
| 12 | 7.23 | 425 | 0 | 0 |
| 13 | 7.45 | 490 | 0 | 0 |
| 14 | 7.87 | 620 | 0 | 0 |
| 15 | 8.12 | 595 | 0 | 0 |
| 16 | 8.32 | 755 | 0 | 0 |
| 17 | 8.7 | 750 | 0 | 0 |
| 18 | 9.27 | 880 | 0 | 0 |
| 19 | 9.81 | 1135 | 0 | 0 |
| 20 | 10.85 | 885 | 0 | 0 |

EXAMPLE 3.

In this Example, the analysis of *P. macroloba* seed extract was pursued from two different aspects. The first was from the point of isolating and identifying the substance(s) responsible for agglutination activity. The second was from the point of isolating and identifying the substance(s) responsible for leucine aminopeptidase activity. The results set forth herein indicate that the same substance(s) are responsible for both agglutination and leucine aminopeptidase inhibition, and for *Ostrina nubilalis* (ECB) mortality in the bioassays.

A. Purification of the Agglutinating Substance(s)

Crude extracts of *P. macroloba* seed were obtained as described above. The extract was separated into fractions using the Rotofor device. The Rotofor fractions were dialyzed and tested for agglutination and ECB mortality. Agglutination and ECB mortality activity were found in the acidic fractions.

Protein assays and SDS-PAGE results indicated that most of the protein contained in the *P. macroloba* extracts focused in the basic Rotofor fractions. When tested or assayed, the basic fractions exhibited little or no agglutination as shown in Example 2, Table 1 and also did not cause significant insect mortality (results not shown).

Rotofor fractions exhibiting agglutination activity were further separated by hydrophobic interaction chromatography using a phenyl Sepharose column and 25 mM sodium phosphate buffer, pH 7. Proteins were eluted with a gradient from 0–6.0 M guanidine hydrochloride in 25 mM sodium phosphate, pH 7.0. Most of the material having agglutination activity eluted late in the guanidine hydrochloride gradient as shown in FIG. 1. Agglutination and insect mortality activity were found in the same fractions.

Figure 2:
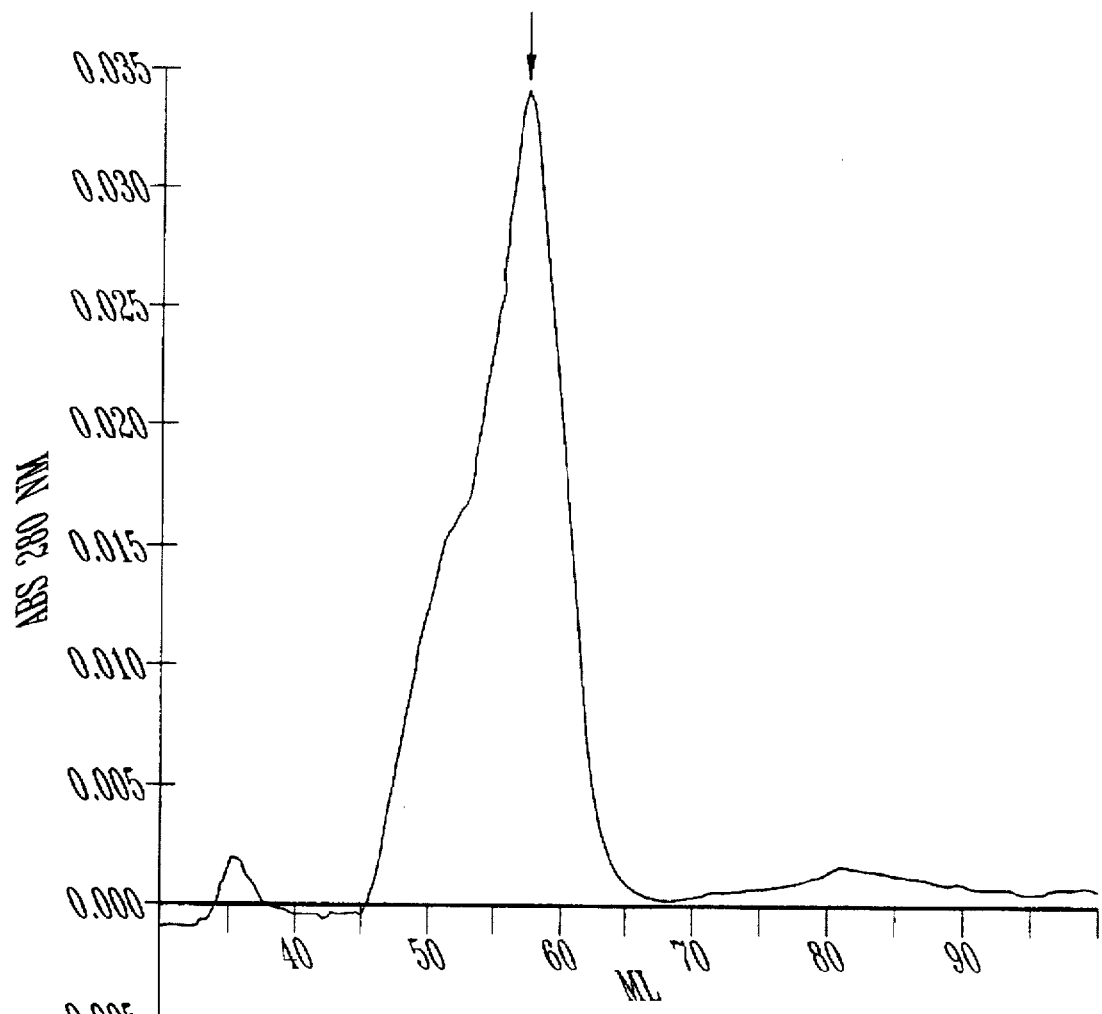
FIG. 2 illustrates the gel filtration of the active substance(s) obtained as shown in FIG. 1, the active component being shown in FIG. 2 as the shoulder and peak indicated by the arrow.

Active fractions after hydrophobic interaction chromatography were pooled, dialyzed, concentrated by lyophilization, and loaded onto a Sepharose 12 gel filtration column. Proteins were eluted with 25 mM sodium phosphate, pH 7.0, containing 150 mM NaCl. The separation was monitored at 280 nm as shown in Fig. 2. Only one major peak, which has a leading shoulder, was eluted from the Sepharose 12 column, suggesting that most of the impurities in the sample were removed during the previous separation steps. Agglutination, insect mortality and leucine aminopeptidase inhibition activity was concentrated in the material of the major peak and shoulder shown in FIG. 2.

Figure 3:
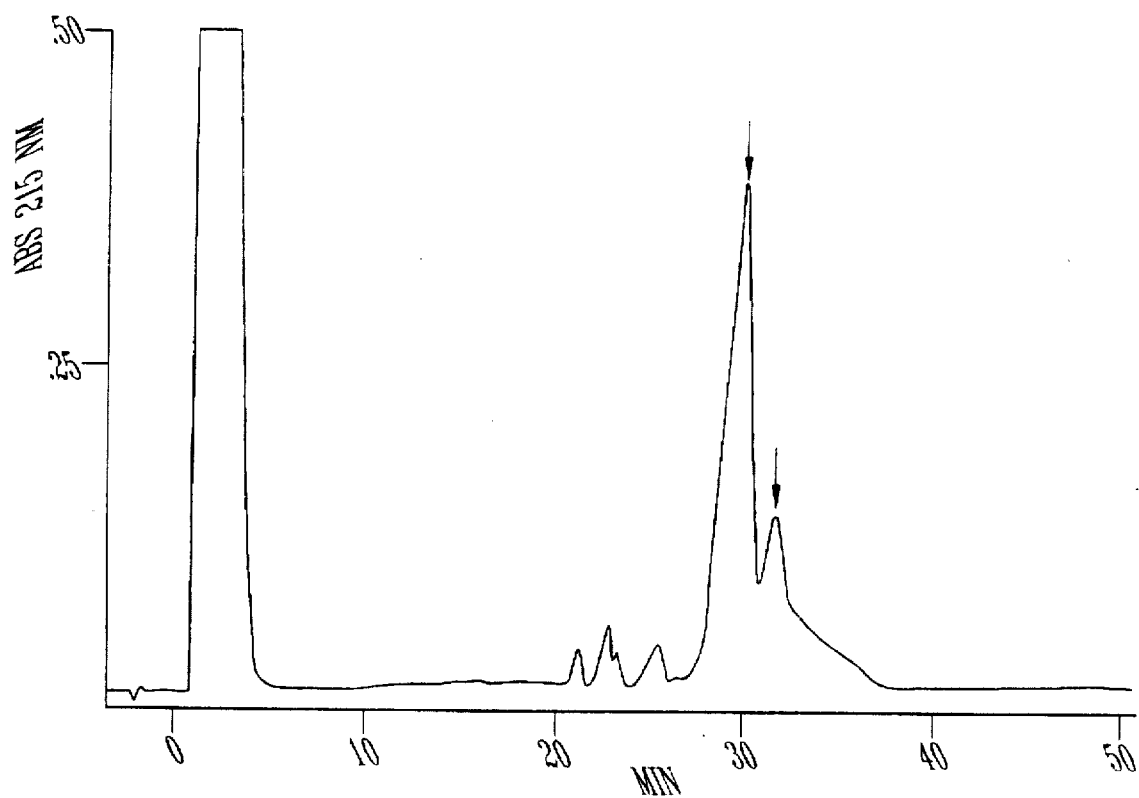
FIG. 3 illustrates the reverse phase high pressure liquid chromatograph (HPLC) of the peak and shoulder substance(s) illustrated in FIG. 2, the active material being indicated by the arrows.

The material in the major peak and shoulder of FIG. 2 was dialyzed, concentrated by lyophilization and subjected to reverse phase chromatography, the results of which are shown in FIG. 3. Disregarding the broad injection peak between about 0–4 min, the reverse phase HPLC shows two major peaks (arrows) which were determined to contain the active agglutinin, LAPI and insect mortality substance(s). However, the activity was at a reduced level compared to the active gel filtration and hydrophobic interaction chromatography fractions described above.

While it was possible, using the chromatograms described above, to isolate and identify substances having agglutination, insect mortality and LAPI activity, attempts to identify these substances using silver or Coomassie Blue stained SDS-PAGE or non-denaturing acrylamide gels were not successful. However, it was noted that on the SDS-PAGE gels, a diffuse clear zone was found close to the position of the bromophenol blue tracking dye in the lanes containing material from Rotofor fractions after the material had been chromatographed and negative $Cu^{++}$ stained. When material from the reverse phase chromatograph of FIG. 3 was likewise subjected to SDS-PAGE, one broad band was found after the bromophenol blue tracking dye. These two sets of results indicate that the active material is of low subunit molecular weight, on the order of 1.5–10 kDa.

Figure 4:
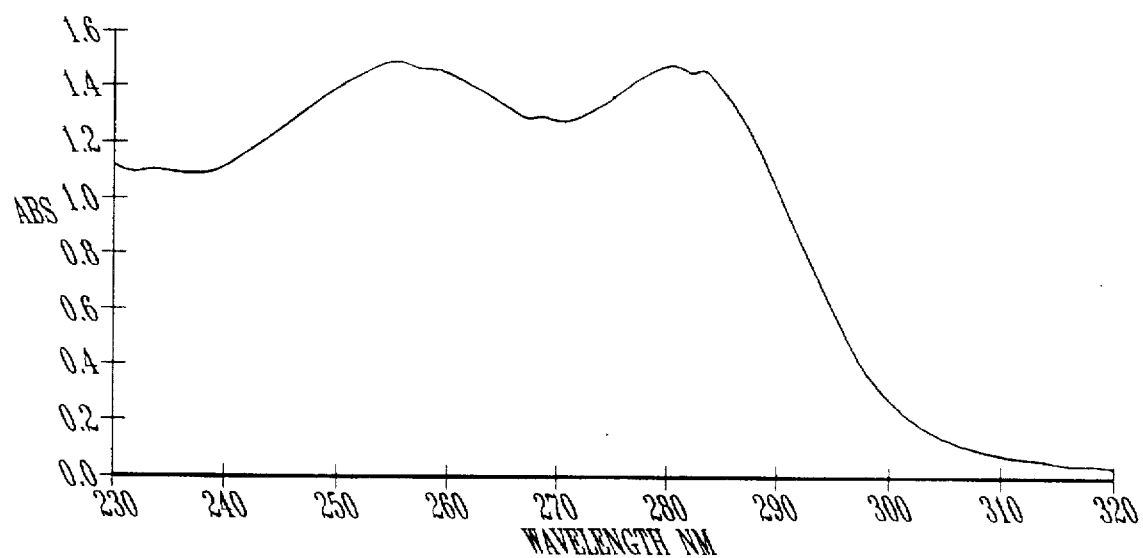
FIG. 4 illustrates the wavelength scan of a preparative SDS-PAGE fraction which eluted after the bromophenol blue marker dye.

In order to obtain larger quantities of the above substance (s), those Rotofor fractions which contain the active material were further purified using preparative tube SDS-PAGE gels. The active material, which eluted immediately after the bromophenol blue marker, was collected in dialysis bags and was analyzed by UV spectrophotometry. The spectrophotometry results, FIG. 4, shows two absorbance maxima at 256 and 280 nm, suggesting that the eluant might contain nucleic acid in addition to protein.

Figure 5A:
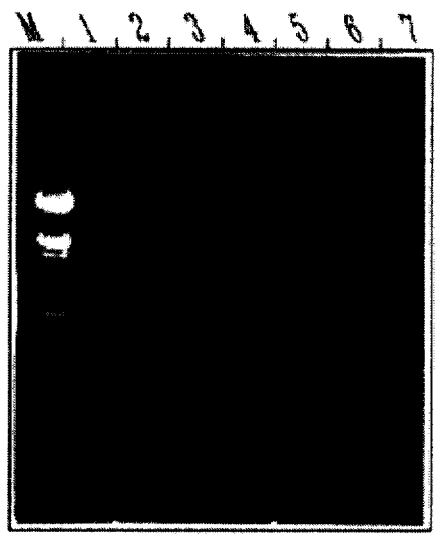
FIG. 5A showing ethidium bromide binding fluorescent material collected after hydrophobic interaction chromatography and FIG. 5B showing ethidium bromide binding fluorescent material after gel filtration.
Figure 5B:
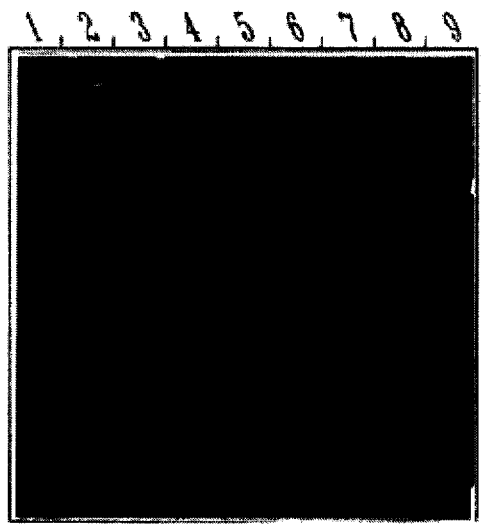
FIG. 5 generally illustrates the ethidium bromide binding fluorescence of the active substance(s) of the invention on an ethidium bromide stained gel.

On the basis of the spectrophotometry results, fractions containing active material which had been subjected to hydrophobic interaction chromatography and gel filtration chromatography were loaded onto agarose gels containing ethidium bromide (EtBr) and subjected to electrophoresis. Under ultraviolet illumination, a fluorescent zone appeared only in lanes which contained agglutinating material as shown in FIG. 5A. Similar results were obtained using Rotofor fractions, ion-exchange chromatography fractions and reverse phase HPLC fractions which were subjected to electrophoresis on agarose gels stained with EtBr. When Rotofor fractions with agglutination activity were loaded onto non-denaturing acrylamide gels, a large fluorescing zone appeared close to the bromophenol blue dye front after staining with EtBr as shown in FIG. 5B.

In order to verify that the EtBr stainable material was indeed the active substance or substances in the various fractions, preparative scale agarose gels and non-denaturing acrylamide tube gels were used to obtain quantities of the material. The material was then tested for agglutination activity and insect mortality. This procedure was facilitated by the weak fluorescence of the material which made it possible to omit staining of the preparative gels with EtBr. Both agglutination activity and insect mortality were found in the fluorescent bands which were collected in both separations. Similar results were obtained when material prepared by agarose gel electrophoresis or non-denaturing acrylamide tube gels was analyzed by reverse phase HPLC. Both peaks bound EtBr and exhibited agglutination activity and insect mortality. No agglutination activity or insect mortality was found in any non-fluorescent material.

The HPLC fractions shown in FIG. 3 were further analyzed and it was determined that the second peak could be converted into the first peak upon rechromatography. Based on results obtained after rechromatography, it appears that the second peak contains the unknown substance which absorbs more strongly at 280 nm and is carried along or conjugated or complexed to the material of the first peak.

B. inhibition of Leucine Aminopeptidase

*P. macroloba* seeds were ground and extracted as described above. In some cases, trypsin inhibitors were removed as described above. Extract was fractionated using the Rotofor apparatus and the fractions tested for the inhibition of digestive enzymes. The acidic fractions from the Rotofor separation were found to inhibit leucine aminopeptidase activity. Using the various separation techniques described above, it was determined that the same substances or substances which affected agglutination and insect mortality would also inhibit leucine aminopeptidase activity. FIG. 6 illustrates the inhibition of 10 μg of porcine aminopeptidase by increasing amounts of the active substance prepared by hydrophobic interaction chromatography. It was determined that 10–50 μg of protein was sufficient to cause 50% LAP inhibition. Similar results were obtained for material purified by preparative electrophoresis or gel filtration.

Biological Assays

Neonate *Ostrina nubilalis* (European corn borer, ECB) larvae were reared on artificial diets containing the leucine aminopeptidase inhibitor (LAPI) obtained from *P. macroloba* as described herein. The LAPI substance(s) may be used as either crude extract or purified as taught herein. The LAPI was either topically applied to the diet surface or incorporated into the diet as taught by Czapla and Lang (26). The culture tray used in the bioassays was divided into treatment groups. One or a plurality of LAPI preparations or fractions from the various separations were screened in each tray, each preparation or fraction being applied to a plurality of cells. Each cell was infested with one or two neonate larvae. A Mylar film with ventilation holes was affixed to the top of each tray to prevent escape and provide air.

For the topical (overlay) assays, a solution containing different concentrations of LAPI was prepared in 0. 1 M phosphate buffered saline (PBS), pH 7.8. Seventy-five microliters of LAPI in buffer solution were pipetted onto the surface of the Stoneville diet medium in each cell. The culture tray was rotated to ensure equal distribution of the inhibitor solution on the diet medium. Neonates were placed on the diet and the cells were sealed as described above. The control was 75 μl of 0.1 M PBS, only, per cell.

For the diet incorporation assays, Stoneville medium was prepared in standard fashion, but with only 90% of the prescribed water. LAPI was added such that the amount in the diet was in the range of 1–5 μg protein per milliliter diet. The control treatment consisted of 0.9 ml PBS buffer added to 8.1 g of medium. The medium was poured into the cells and the cells were then infested and covered as described above. Insect weights (Weight or Avg. Wt.) were determined 7–10 days after placing the neonates on the diet. The results of the assays are given in the tables.

Table 2 gives the results of the LAPI substance(s) on European corn borer larvae in topical assays. The percent mortality was determined at the end of a standard 7-day assay. The relative agglutination results were obtained using rabbit blood and standard agglutination procedures. The designation Rotofor/Q5 # X-Y indicates that the sample being used was Rotofor fractions 1–5 (see Table 1) which were subsequently chromatographed on a Sepharose Q5 column using standard techniques and isolated as fractions No. X to Y. The agglutination symbols +++ and ++ signify increasing agglutination titres, respectively. The results clearly indicate that the substance(s) responsible for leucine aminopeptidase inhibition is also responsible for insect mortality and agglutination activity.

TABLE 2

Effects of *P. macroloba* Substances on ECB Larval Mortality Using an Overlay Assay.

| Fractions | Diet Protein (μg/ml) | Cell Protein (μg/ml) | % Mortality | Relative Agglutination |
|---|---|---|---|---|
| Prep 1 | | | | |
| A | 26.1 | 2.6 | 100 | ++ |
| B | 19.4 | 1.9 | 100 | +++ |
| C | 14.3 | 1.4 | 100 | ++ |
| Prep 2 | | | | |
| A | 30.9 | 3.1 | 100 | +++ |
| B | 21.7 | 2.2 | 100 | +++ |
| C | 15.8 | 1.6 | 100 | ++ |
| Prep 3 | | | | |
| A | 51.7 | 5.1 | 100 | +++ |
| B | 19.0 | 1.9 | 69 | ++ |

Notes:
Prep 1: A = Rotofor/Q5 Sepharose, fractions 9–11.
B = Rotofor/Q5 Sepharose, fractions 12–14.
C = Rotofor/Q5 Sepharose, fractions 15–18.
Prep 2: A = Rotofor/Q5 Sepharose, fractions 7–11.
B = Rotofor/Q5 Sepharose, fractions 12–14.
C = Rotofor/Q5 Sepharose, fractions 15–18.
Prep 3: A = Rotofor/Q5 19–22/Superose, 12 fraction 12
B = Rotofor/Q5/Superose, 12 fraction 13.

FIG. 7 graphically illustrates the toxicity of the active substance(s) extracted from *P. macroloba* to European corn borer larvae. Crude extract is material which has particulate matter removed. HIC signifies extract which has been purified through hydrophobic interaction chromatography as described herein. PAG material that has been purified using preparative, non-denaturing acrylamide gel electrophoresis as described herein. Toxicity tests were performed using material topically applied to diet as described herein.

The results indicate that the agglutinating, leucine aminopeptidase inhibiting material obtained from P. macroloba is highly toxic to ECB. The toxicity is comparable to that of B. thuringiensis.

Amino Acid Analyses

Table 3 gives the amino acid analysis of the substance disclosed herein which exhibits agglutination activity, ECB toxicity and leucine aminopeptidase inhibition. Column A represents the calculated amino acid values obtained in one early analysis. Columns B, C, D and E represent four additional preparations which were analyzed, and the amino acid values for these analyses are reported as integers for simplicity. The analytical results for B, C, D and E were averaged to reduce error. The averaged results are shown in the Average column (Avg). The active material represented by the indicated peaks of FIG. 3 were analyzed. In all analyses, the most abundant residues were glycine, serine, alanine, threonine, aspartic acid and glutamic acid. All analyses indicated the absence of or low levels of cysteine, methionine, tryptophan, hydroxyproline and hydroxylysine residues. On the basis of all the analytical results, including the amino acid analyses, the active substance(s) obtained from *P. macroloba* appear to comprise a component which is fluorescent and binds EtBr, a low molecular weight protein or proteinaceous component which has the indicated amino acid analysis, and sugars.

Table 4 gives multiple amino acid analyses representing repeat separations of the substance disclosed herein which exhibits agglutination activity, ECB toxicity and leucine aminopeptidase activity after treatment in solution with HF (hydrofluoric acid) at 0° C., by methods known in the art, to remove carbohydrates. These analyses, although indicating a greater number of amino acids than the data in Table 3, are nonetheless consistent with Table 3 and serve to indicate that the active substance derived from *P. macroloba* is capable of forming multimers and/or adducts with other substances such as proteinaceous substances, carbohydrates and sugars which may be present with the active substance. The fact that these multimers or adducts persist through various separatory and analytical procedures indicates that they are of at least moderate strength and stability, and further indicates and explains why active substances of different molecular weight may have insecticidal properties as is indicated herein.

Treating the active substance with NaOH, nucleases or proteases did not destroy the fluorescence of EtBr stained gels. However, NaOH and protease treatment did lead to a change in mobility. Treatment with chlostripan argC-protease did not change the retention time on reverse phase HPLC.

Extracting active fractions separated by gel filtration chromatography, anion exchange chromatography or preparative Rotofor fractions with phenol and chloroform resulted in the loss of most of the fluorescence in the aqueous layer. A faint residual fluorescence remained which could be due to residual material or some substance derived from the original fluorescent substance.

TABLE 3

Amino Acid Analysis of Pentin-2

| | A^ | B* | C* | D* | E* | Avg. |
|---|---|---|---|---|---|---|
| Aspartate | 2.13 | 2 | 3 | 3 | 4 | 3 |
| Threonine | 4.09 | 4 | 4 | 2 | 2 | 3 |
| Serine | 5.18 | 5 | 5 | 4 | 4 | 4.5 |
| Glutamic | 4.27 | 4 | 4 | 3 | 4 | 3.75 |
| Glycine | 9.23 | 9 | 7 | 6 | 4 | 6.5 |
| Alanine | 3.32 | 3 | 4 | 4 | 4 | 3.5 |
| Valine | 1.85 | 2 | 2 | 2 | 3 | 2.25 |
| Methionine | 0 | 0 | 0 | 0 | 0 | 0 |
| Isoleucine | 0.97 | 1 | 1 | 1 | 2 | 1.25 |
| Leucine | 1.33 | 1 | 2 | 2 | 3 | 2 |
| Tyrosine | | 0 | 1 | 1 | 1 | 0.75 |
| Phenylalanine | | 0 | 2 | 1 | 2 | 1.25 |
| Lysine | 5.59 | 5 | 8 | 5 | 3 | 5.25 |
| Histidine | | 0 | 1 | 1 | 1 | 0.75 |
| Arginine | 3.08 | 3 | 2 | 2 | 2 | 2.25 |
| Proline | | | | | 2.25 | 0.625 |
| Total Residues | | 39 | 46 | 36 | 41.5 | 40.625 |

Note:
^ = Early detailed analysis of Pentin-2.
* = Analyses for different preparations of Pentin-2.
Avg. = average number of amino acids in B, C, D, and E.

TABLE 4

Amino Acid Analysis of Carbohydrate-Free Pentin-2

| | F | G | H | I | J | Avg. |
|---|---|---|---|---|---|---|
| Aspartate | 4 | 5 | 5 | 5 | 5 | 4.8 |
| Threonine | 2 | 5 | 2 | 3 | 2 | 2.8 |
| Serine | 9 | 5 | 4 | 6 | 8 | 6.4 |
| Glutamic | 4 | 6 | 6 | 6 | 9 | 6.2 |
| Glycine | 25 | 16 | 15 | 17 | 11 | 18.8 |
| Alanine | 6 | 5 | 6 | 6 | 4 | 5.2 |
| Valine | 3 | 3 | 3 | 4 | 3 | 3.2 |
| Methionine | 1 | 0 | 0 | 0 | 0 | 0.2 |
| Isoleucine | 1 | 1 | 1 | 2 | 2 | 1.4 |
| Leucine | 1 | 2 | 3 | 3 | 3 | 2.4 |
| Tyrosine | 1 | 0 | 1 | 1 | 2 | 1 |
| Phenylalanine | 1 | 0 | 1 | 1 | 2 | 1 |
| Lysine | 2 | 4 | 4 | 4 | 4 | 3.6 |
| Histidine | 0 | 0 | 0 | 0 | 0 | 0 |
| Arginine | 1 | 2 | 3 | 3 | 3 | 2.4 |
| Proline | 0 | 3 | 5 | 0 | 3 | 2.2 |
| Cysteine | 1 | 2 | 0 | 0 | 0 | 0.6 |
| Total Residues | 62 | 59 | 59 | 61 | 615 | 60.4 |

Note: The amino acid analyses F–J of Table 4 were carried out using material which had been treated, by methods known in the art, with HF to remove carbohydrates.
Avg. = average number of amino acids in F through J.

During amino acid analysis, a ninhydrin positive, unidentified component was detected. This component appears to be relatively abundant. This component does not correspond to any of the unusual amino acids such as hydroxyproline. Based on its peak, it is more abundant than the most abundant amino acid present in the analyses given above. The fact that it is ninhydrin positive suggests that it is an amino acid or an amino acid derivative.

It is also noted that an amino acid analysis gives a ratio of the various amino acids present in a substance. In the actual substance, the amino acids may actually be present as some multiple of that ratio. This fact also helps to explain why by some techniques the molecular weight may appear to be in the range 1.5–10 kDa, and by other techniques the molecular weight may appear in the range 40–60 kDa., or in the range 10–40kDa.

The data and descriptions which have been presented herein are for the purpose of illustrating the invention and are not to be taken as limiting the scope of the invention. Other tropical forest plants, or plants from other locations, can be evaluated with regard to their containing the LAPI inhibitory and insecticidal compounds described herein. It is within the scope of this invention that those skilled in the art, using the teachings herein, will be able to extract, purify and isolate, from the plants of tropical forests and other locations, LAP inhibitors analogous to that which is described herein.

Transgenic Uses

Those skilled in the art of plant genetics, using the genetic techniques which have been developed over the last several decades, can transfer the gene encoding for the production of the leucine aminopeptidase inhibitor (LAPI) of the present invention into the genetic code of food and fiber crops such as corn, soybeans, squashes, cotton and similar food and fiber crops. Expression of the gene encoding the *P. macroloba* aminopeptidase inhibitor will enable the crops to produce the LAPI compound and thus protect themselves against attack by insect pests such as those described herein. Methods for producing transgelic plants are well known to those skilled in the art. For example, one may use, among others known to those skilled in the art, the teachings of Koziel et al., *BIO/TECHNOLOGY* 11: 194 200 (1993), Vaeck et al., *Nature* 327: 33–37 (1987), Hilder et al., *Transgenic Research* 4: 18–25 (1995) and *Nature* 330: 160–167 (1987), and Johnson et al., *Proc. Natl. Acad. Sci.* 86: 9871–9875, all of which are incorporated herein by reference. The sequence of the LAPI inhibitor and the gene which encodes it may be determined by methods, automated or manual, known to those skilled in the art.

While the gene encoding the LAPI substance of the claimed invention may be introduced into plants using known techniques, care must be taken that such gene is expressed. For example, Ryan et al. (24) reported on the presence of proteinaceous trypsin inhibitors and lectins in the seeds of a number of leguminous plants and suggested that these proteins may play a role in the plants' defenses against insect attack. Hilder et al. (18) introduced the Bowman-Birk trypsin inhibitor gene from soybeans into tobacco plants and showed that the transgenic plants were able to resist damage from a lepidopteran insect. Likewise, transformation and expression of other trypsin inhibitor genes such a Potato TI I and II also resulted in transgenic plants which showed resistance to insect attack. However, transgenic plants which contained an unexpressed gene were susceptible to insect attack (20). Consequently, in order to have pest protection, a plant must not only contain the protective gene or genetic sequence, but must also express it. That is, the transgenically inserted gene must be producing, or be capable of producing upon pest attack, the inhibitor or defensive agent. Furthermore, the choice of substance to be inserted into a plant species for pest control is also critical. Christeller et al. (15), using trypsin inhibitors from different plant species, have demonstrated that TI's have considerably different inhibitory constants ($K_i$ values).

We claim:

1. A plant-derived trypsin inhibitor free composition which exhibits leucine aminopeptidase inhibition activity, hemagglutination activity and increased insect mortality rates, said composition comprising at least one substance suitable for use as an insecticide and obtained from *Pentaclethra macroloba* by the steps comprising the aqueous extraction of *Pentaclethra macroloba* seeds to obtain a crude extract having leucine aminopeptidase inhibition activity, hemagglutination activity and increased insect mortality, and purifying the crude extract by separatory techniques to remove trypsininhibitors and to obtain at least one substance which has a minimum molecular weight in the range 1.5–10 kDa.

2. The composition according to claim 1, wherein said substance is a unit of approximately 41 amino acid residues and a fluorescent component; said amino acids being approximately: 3 aspartate, 3 threonine, 4-5 serine, 3- 4 glutamic, 6-7 glycine, 3- 4 alanine, 2-3 valine, 1-2 isoleucine, 2 leucine, 0-1 tyrosine, 1.-2 phenylatanine, 5-6 lysine, 0-1 histidine, 2-3 arginine and 0-1 proline.

3. The composition according to claim 2, wherein said composition is an insecticide against an insect pest selected from the group consisting of European corn borer, a plurality of Diabrotica species, corn. earworm, cowpea weevil and similar insect pests.

4. The composition according to claim 2, wherein said amino acid containing substance therein forms a multimeric species with itself, or a complex, conjugate, adduct, multimeric or similar species between itself and one or a plurality of substances selected from the group consisting of a fluorescent substance, a proteinaceous substance and sugars, said multimer, complex, conjugate, adduct and similar species having a molecular weight to about 60,000 Daltons, and having leucine aminopeptidase inhibitory, hemagglutination and insect mortality activity.

5. The composition according to claim 4, wherein said composition is an insecticide against an insect pest selected from the group consisting of European corn borer, a plurality of Diabrotica species, corn earworm, cowpea weevil and similar insect pests.

6. A trypsin inhibitor free composition suitable for protecting plants against the European corn borer, said composition comprising at least one substance extracted from *Pentaclethra macroloba* seeds which has an amino acid containing component and a fluorescent component; exhibits leucine aminopeptidase inhibition activity, hemagglutination activity, and increases the mortality rate of European corn borer larvae; and by analysis has approximately 41 amino acids comprising 24 aspartate, 2-4 threonine, 4-5 serine, 3-4 glutamic, 6-9 glycine, 3-4 alanine, 2-3 valine, 1-2 isoleucine, 1-3 leucine, 0-1 tyrosine, 1-2 phenylalanine, 5-8 lysine, 0-1 histidine, 2-3 arginine, 2-3 proline, and no methionine, cysteine, tryptophane, hydroxyproline or hydroxylysine.

7. A method of protecting plants against insect attack, said method comprising the steps of
(a) extracting *Pentaclethra macroloa* seed with an aqueous solution to obtain a composition hemagglutination activity, leucine aminopeptidase inhibitory activity and increase insect mortality; and
(b) topically or systemically applying an effective amount of said composition, either in crude form or after purification by separatory techniques to remove trypsin inhibitors and proteins soluble in basic medium, to said plants to protect said plants against insect attack;
wherein said composition contains at least one substance with a minimum molecular weight in the range 1.5 to 10 kDa.

8. A method of protecting corn plants against the European corn borer, said method comprising the steps of
   (a) extracting *Pentaclethra macroloba* seed with an aqueous solution to obtain a composition which has hemagglutination activity, leucine aminopeptidase inhibitory activity and increase insect inortality; and
   (b) topically or systemically applying an effective amount of said composition, either in crude form or after purification by separatory techniques to remove trypsin inhibitors and proteins soluble in basic medium, to corn plants to protect said plants against European corn borer; said substance having a unit of approximately 41 amino acid residues, said amino acids being approximately: 3 aspartate, 3 threonine, 4-5 serine, 3-4 glutamic, 6-7 glycine, 3-4 alanine, 2-3 valine 1-2 isoleucine, 2 leucine, 0-1 tyrosine, 1-2 phenylalanine, 5-6 lysine, 0-1 histidine, 2-3 arginine and 0-1 proline; said substance having a minimum molecular weight in the range 1.5–10 kDa and capable of forming a multimeric species with itself, or a complex, conjugate, adduct, multimeric or similar species between itself and one or a plurality of substances selected from the group consisting of a fluorescent substance, a proteinaceous substance and sugars, wherein said multimer, complex, conjugate, adduct and similar species has a molicular weight to about 60,000 Daltons.

* * * * *

UNITED STATES PATENT AND TRADEMARK OFFICE
CERTIFICATE OF CORRECTION

PATENT NO : 5,756,661
DATED : May 26, 1998
INVENTOR(S): Karel R. Schubert, et al.

It is certified that error appears in the above-identified patent and that said Letters Patent is hereby corrected as shown below:

Cover Page - should read:
[73] Assignee(s): Pioneer Hi-Bred International, Inc.
Des Moines, Iowa and The Board of Regents of the University of Oklahoma
Norman, Oklahoma Signed and Sealed this Twenty-seventh Day of June, 2000

Attest:

Q. TODD DICKINSON

*Attesting Officer*  *Director of Patents and Trademarks*